United States Patent [19]

Owen

[11] 4,249,131
[45] Feb. 3, 1981

[54] METHOD AND APPARATUS FOR MEASURING ELECTROSTATIC CHARGE DENSITY

[75] Inventor: Thomas E. Owen, San Antonio, Tex.

[73] Assignee: The United States of America as represented by the Secretary of Commerce, Washington, D.C.

[21] Appl. No.: 29,242

[22] Filed: Apr. 11, 1979

[51] Int. Cl.³ .......................................... G01N 27/60
[52] U.S. Cl. .................................... 324/452; 324/457; 324/464
[58] Field of Search ........................ 324/452, 457, 464

[56] References Cited

U.S. PATENT DOCUMENTS

| | | | |
|---|---|---|---|
| 2,969,503 | 1/1961 | Bustin | 324/457 |
| 3,526,828 | 9/1970 | Whitby | 324/464 |
| 3,824,454 | 7/1974 | Stern | 324/457 |
| 4,117,715 | 10/1978 | Hoenig | 324/452 |

FOREIGN PATENT DOCUMENTS

237409 12/1969 U.S.S.R. ................................... 324/452

Primary Examiner—Michael J. Tokar
Attorney, Agent, or Firm—Eugene J. Pawlikowski; Alvin J. Englert

[57] ABSTRACT

An apparatus and method for momentary sampling of an atmosphere to determine electrostatic charge density is disclosed. A nonconductive elongated sampling tube is inserted into the area to be sampled. An intake valve on the end of the elongated sampling tube is opened momentarily and a small sample of the atmosphere to be sampled is moved through the intake valve and the elongated sampling tube into an isolated metallic inner cylinder filled with metallic wool. An outer metallic cylinder is located concentrically around the inner cylinder and is electrically isolated therefrom except for a single discharge path through an electronic control package. Current flow between the inner cylinder and outer cylinder is measured by a sensitive ammeter in the electronic control package and is electronically converted to indicate charge density in coloumbs/meters³.

24 Claims, 13 Drawing Figures

METHOD AND APPARATUS FOR MEASURING ELECTROSTATIC CHARGE DENSITY

This invention was developed by Southwest Research Institute under Contract No. 5-38044 with the Maritime Administration, United States Department of Commerce.

BACKGROUND OF THE INVENTION

This invention relates to a method and apparatus for measuring electrostatic charge density and, more specifically, to an apparatus that may be used to determine the charge density of atmospheres in ship tank enclosures, such as crude oil tankers or bulk cargo carrier ships.

BRIEF DESCRIPTION OF THE PRIOR ART

With the increase in size of bulk carrier ships and the recent introduction of the "supertankers", washing and slack tank sloshing result in electrostatic charged mist being created in the tanks of the ship. As a result of explosions onboard ship occurring in the late 1960's, different safety measures were introduced to eliminate possible explosions caused by electrostatic charge. One common method was to use inert gas from the boiler flue after the removal of soot particles and inject the inert gas into the tank of the ship. The inert gas would then be used to either displace the existing gas in the tank or to dilute the gas so that it would not ignite.

The present invention was spurred by catastrophic explosions onboard supertanks that were caused as a result of tank washing having created at electrostatically charged flammable tank atmosphere. In further studies, it was determined that electrostatically charged atmospheres were created during washing by formation of liquid slugs of sufficient size to create an electric arc discharge that could ignite flammable atmospheres. The present invention is designed for the testing of electrostatic charge in the atmosphere of the tank to determine if it has reached dangerous proportions. In taking such a sample, it is important that the atmosphere of the tank not be disturbed more than absolutely necessary to take the measurement. Many times the tank cannot be entered by the persons making the measurement; therefore, the present invention uses a nonmetallic sampling tube that may be inserted through any particular opening for extracting the sample from the tank to determine the charge density. As an alternative, permanent extraction points may be mounted in the tank of a ship. Current generated as a result of the momentary sample taken through the sampling tube may then be converted by appropriate electronic circuitry to give the approximate charge density of the ship's tank.

The closest prior art of such a charge density meter known to applicant is U.S. Pat. No. 4,117,715 issued on Oct. 3, 1978 to Stuart A. Hoenig. In the Hoenig patent, the apparatus simply determines the polarity of the charge of the particles. As shown in Hoenig, particles are sized from the atmosphere by selectively graded filter stages which are arranged in a cascade manner along the air flow path. Hoenig does not show how to measure and determine the approximate electrostatic space charge density of sampled air. Also, there is no assurance that the particles retrieved by a filter (which are of a particular size range) represent the total charge density of the atmosphere to even give the correct polarity, much less the electrostatic space charge density. The present invention in no way discriminates between particle sizes in measuring the charge density of the sampled volume.

SUMMARY OF THE INVENTION

It is an object of the present invention to provide a method and apparatus for determining the approximate electrostatic charge density of a particular atmosphere.

It is a further object of the present invention to provide a mechanical means for extracting a sample of atmosphere from an enclosed area without electrically disturbing the enclosed atmosphere a significant amount.

It is still another object of the present invention to provide a means for taking a sample of electrostatically charged atmosphere and measuring current flow created as a result of the electrostatic charge to determine the electrostatic charge density of the atmosphere.

It is yet another object of the present invention to provide a means for electronically converting current flow generated as a result of an electrostatically charged sample to determine the electrostatic charge of the sampled volume.

A sampling tube made from an electrically nonconductive material is inserted into an enclosed atmosphere. Initial flow through the sampling tube is from a noncharged atmosphere, other than the enclosed atmosphere to be sampled, and through a charge density meter. The charge density meter includes concentric cylinders with the charge of the sampled atmosphere being transmitted to one of the cylinders by a metallic wool filler to create essentially a charge on the capacitor formed by the concentric cylinders. By measuring current flow from the charge plate (inner cylinder) of the capacitor to the grounded plate (outer cylinder), a current flow proportionate to the charge density is created. By electronically measuring the current flow through an ammeter, a signal proportional to the charge density is created. By the use of appropriate electronic logic controls, including timers, event detectors, latches, visual readouts, etc. with an appropriate power supply, a momentary sample can be converted into an approximation very close to the actual electrostatic charge density of the sampled atmosphere.

In the method of operation of the preferred embodiment, the sampling tube would be inserted through an opening into an enclosed area to measure the charge density of the atmosphere. By the opening of a sampling intake valve for a predetermined period of time, a sample of the atmosphere from the enclosed area is transferred via the sampling tube to an inner cylinder having the metallic wool filler therein. By measuring the current flow caused by the sample volume from the inner cylinder through an electronic package to the outer cylinder, the electrostatic charge density of the sampled atmosphere is approximated. A vacuum is created in the sampling tube by any appropriate means, such as a commercial vacuum cleaner/blower with the flow rate being accurately monitored. Once the charge created on the inner cylinder by the metallic wool filler has stabilized, the current measurement may be taken and permanently latched into a memory or simultaneously recorded.

It may be necessary to fine tune the sampling tube to insure a constant air flow therethrough prior to, during and after the taking of the sample. Also, the electronics of the charge density meter would need to be calibrated against a sample having a known electrostatic charge density.

DESCRIPTION OF THE PREFERRED EMBODIMENT

In cargo ships, such as crude oil tanks, a suspended charge mist may result from pressure jet spray washing processes using either sea water or possibly the crude oil product being transported in a tank as the cleaning agent. Hydrocarbon gases released from the contaminating crude oil materials in the tank may produce a flammable atmosphere which can be ignited by an electric arcing phenomena caused by the charged mist contained within the tank of the ship.

The present invention provides an instrument capable of directly sensing and measuring the electrostatic space charge density in the tank of the ship. The instrument is capable of safely and reliably sampling the charged mist contained in the potentially explosive atmosphere of the tank. A minimum amount of the charged aerosal mist inside of the tank is used for the test, thereby making the minimum amount of disturbance to the electrostatic charge conditions of the tank atmosphere.

Figure 1A:
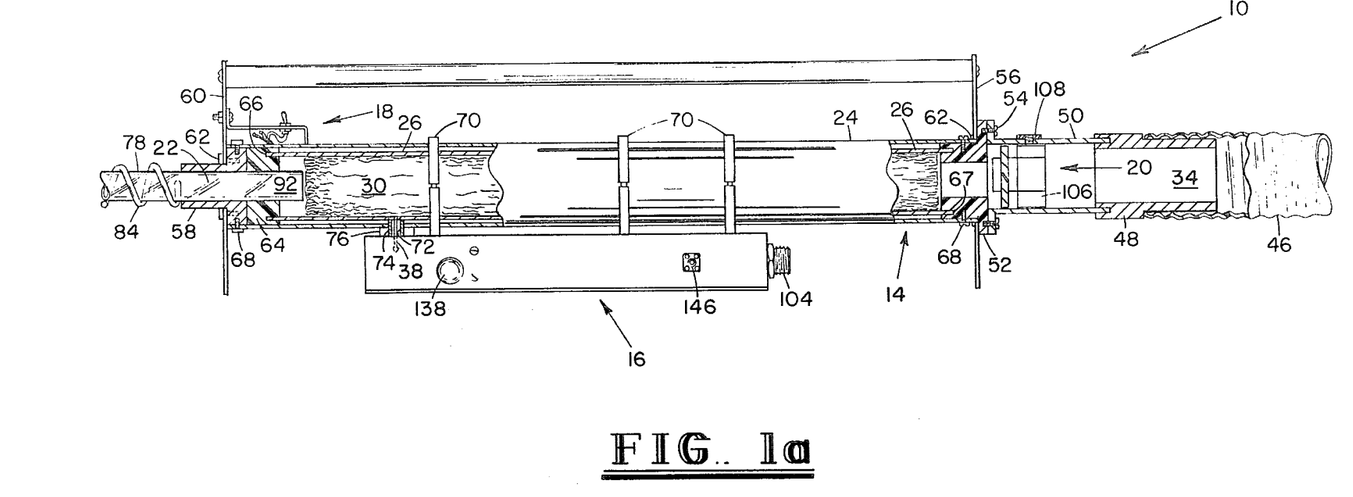
FIGS. 1a and 1b are elevated, partially sectional side views of the charge density meter and sampling tube disconnected from the power source, vacuum source, and monitoring means.
Figure 1B:
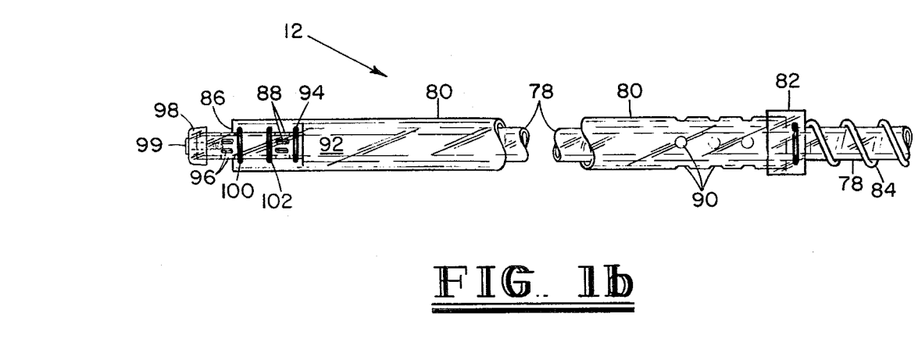

Referring to FIGS. 1a and 1b, there is shown an electrostatic charge density meter represented generally by reference numeral 10. The electrostatic charge density meter consists generally of a sampling tube 12, a capacitive measuring chamber 14, an electronics control package 16, indicator panel 18, air flow sensor 20, all of which are connected to a suitable vacuum source, power source, and monitoring apparatuses which will be described in more detail hereinafter.

Figure 2:
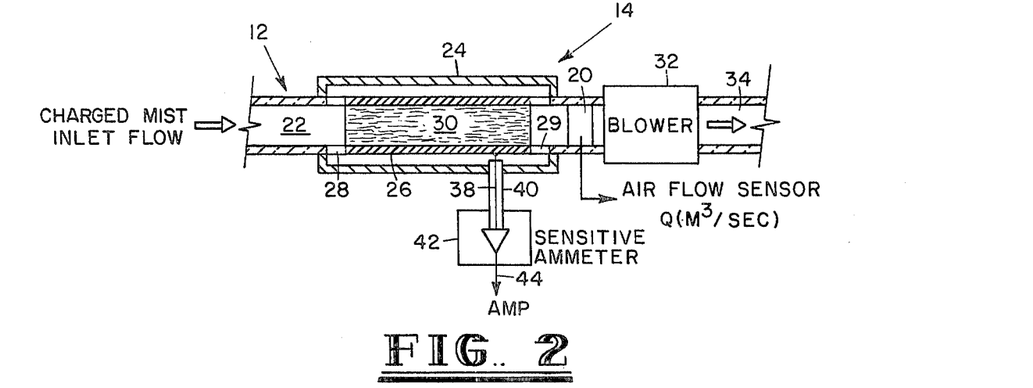
FIG. 2 is a simplified cross-sectional view of basic components of the charge dneisty meter as may be used in FIG. 1.

FIG. 2 shows a simplified view of FIG. 1. A charged mist is received through inlet flow passage 22 of sampling tube 12. The capacitive measuring chamber 14 includes an outer metal shield 24, commonly called the outer cylinder, which is connected to ground. Inside of the outer cylinder is an inner cylinder 26 which receives the flow from inlet flow passage 22. The inner cylinder 26 is electrically isolated by insulators 28 and 29. Inside of the inner cylinder 26 is located metallic wool filler 30, such as stainless steel wool. A blower 32 causes a continual flow of the charged mist through the inlet flow passage 22, the inner cylinder 26 of the capacitive measuring chamber 14, and out an outlet flow passage 34. The air flow sensor 20 monitors the flow of the charged mist through the capacitive measuring chamber 14.

An electrical connection with the inner cylinder 26 is provided by wire 38 received through outer cylinder 24 via insulation/isolation protection 40 into a sensitive ammeter 42. The sensitive ammeter 42 has an output 44 given in amps that is related to the electrostatic charge density of the charged mist received inside of inner cylinder 26. By proper monitoring of the output 44, the electrostatic charge density can be determined. The current at the output 44 is determined as follows:

$$I = k(dq/dt)$$

where:
q = electric charge entering the capacitive measuring chamber 14 (coulombs);
k = charge collection effectiveness of the metallic wool filler 30.

The total charge can be expressed in terms of the charge density and volume flow of the charged mist as follows:

$$q = \rho V$$

where:
$\rho$ = charge density of the mist (coulombs/meters$^3$);
V = mist volume (meters$^3$).

For a constant charge density, the current flow produced by the charge on the metallic wool filler can be expressed as follows:

$$I = k\rho(dV/dt)$$

where: $dV/dt = Q =$ mist flow rate (meters$^3$/sec).

Thus, the charged density is proportional to the measured current by the following expression:

$$\rho = I/(kQ)$$

The particular apparatus has a significant advantage over prior devices because it only takes a momentary sample of a minimum quantity of the charged mist, thereby it does not remove a significant portion of the charged mist from the tank. The sample or slug of the charged mist is moved through the capacitive measuring chamber 14 by means of an uncharged air flow stream.

Referring now to FIG. 1 in combination with FIG. 2, a more detailed explanation of one possible configuration of the electrostatic charge density meter 10 is given. A vacuum exhaust source (pictorially shown as blower 32 in FIG. 2) is connected through a flexible hose 46 through an adapter 48. The adapter 48 is connected through flange connector 50 to insulating flange connector 52 by means of screws 54. Insulating flange connector 52 is in turn connected to rear mounting plate 56. Rear mounting plate 56 is received inside of outer cylinder 24 in the same manner as intake flange 58 is received through front mounting plate 60 into outer cylinder 24. The insulating flange connector 52 and the intake flange 58 are connected to rear mounting plate 56 and front mounting plate 60 by means of screws 62. Inside of the outer cylinder 24, insulating flange connector 52 and intake flange 58 abut insulator 64 to securely hold inner cylinder 26 in position inside of grooves 66 of insulator 64 and grooves 67 of insulating flange connector 52. By maintaining the inner cylinder 26 inside of the grooves 66 and 67, the inner cylinder 26 is electrically isolated from the outer cylinder 24. The insulating flange connector 52 and the intake flange 58 are attached to the outer cylinder 24 by means of screws 68.

Inside of the inner cylinder 26 is located the metallic wool filler 30 which maintains electrical conductivity with the inner cylinder 26. The electronic control package 16 mounted below the outer cylinder 24 by means of brackets 70 is electrically connected by wire 38 through an opening 72 in the outer cylinder 24 to the inner cylinder 26. The electrical connection has an insulating sleeve 74 therearound and is electrically isolated by means of shielding 76.

The sampling tube 12 is made from a nonmetallic, nonconductive material, such as a clear plastic, and includes an inner tube 78 received in an air tight manner inside of intake flange 58. Slideably mounted on the inner tube 78 is an outer tube 80. Retaining ring 82 slideably seals the rear portion of outer tube 80 to inner tube 78. Spring 84, which is located between retaining ring 82 and intake flange 58, is maintained under compression thereby continually urging the outer tube 80 to the left.

Figure 3:
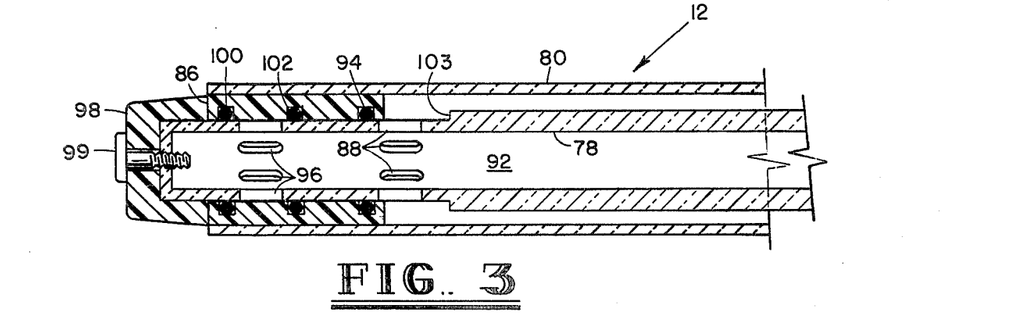
FIG. 3 is an enlarged cross-sectional view of the sampling valve on the end of the sampling tube shown in FIG. 1.

Referring to FIG. 1b in conjunction with FIG. 3, on the lefthand end of the outer tube 80 is an intake retaining ring 86 that slideably seals with the inner tube 78, and is bonded to the outer tube 80 in an air tight manner. Circulating openings 88 allow air to be drawn in through air intake holes 90, through the space between the inner tube 78 and the outer tube 80, through the circulating openings 88, and through the center flow passage 92 (inlet flow passage 22) of the inner tube 78 into and through the capacitive measuring chamber 14 by means of the vacuum source. By moving the outer tube 80 to the right, the circulating openings 88 are closed by seal rings 94 and 102, and the intake sampling passages 96 are opened by sliding past seal ring 100. Further, seal ring 102 insures that the circulated air does not mix with the portion being sampled. Cap 98, which is held in position by screw 99, controls the leftward movement of outer tube 80, and may be used to regulate circulating air flow rates to insure substantially equal flow through either circulating openings 88 or intake sampling passages 96. Shoulder 103 controls rightward movement of outer tube 80.

METHOD OF OPERATION OF PREFERRED EMBODIMENT

The electronic control package 16 is connected to a suitable power supply and digital readout meter via connector 104 as will be explained in more detail subsequently. Air flow through the electrostatic charge density meter may be provided by commercially available industrial vacuum cleaners; however, the air flow is monitored by air flow sensor 20 by means of turbine 106 generating a pulsed output at turbine output 108.

First, the sampling tube 12, which is normally several feet long, is inserted into a tank containing a charged aerosol mist. A read switch on the indicator panel 18 is pushed which turns on a light emitting diode to be viewed by the operator. Next, the intake sampling passages 96 are opened by pulling back (to the right) on the outer tube 80 of the sampling tube 12 for approximately three seconds.

The charged aerosol mist is drawn in through the intake sampling passages 96, center flow passage 92, into the capacitive measuring chamber 14. The electronic circuitry contained in the electronics control package 16 detects the presence of a charged mist and makes the measurement of current flow automatically. Once the measurement has been completed, the light emitting diode turns OFF and the outer tube 80 can be released. A voltage reading on the digital readout meter will indicate a value proportional to the charge density of the aerosol mist.

Figure 4:
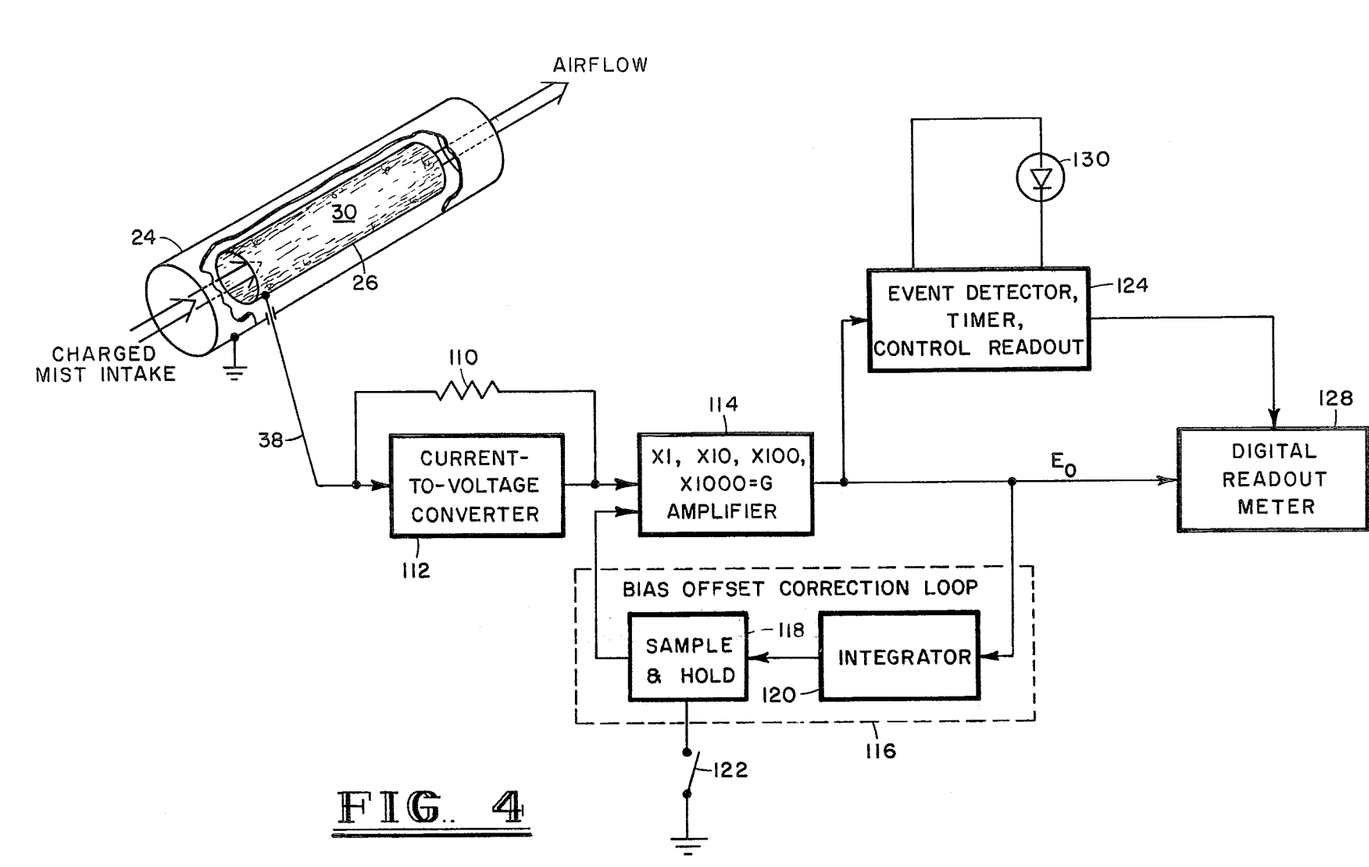
FIG. 4 is a smplified block electrical diagram of a momentary sampling charge density meter that is partially shown in FIG. 1.

Referring to FIG. 4 in conjunction with the following description, the general operation of the electronic circuitry that performs the actual measurements and the relationships from which the charge density is calculated is described. The charged aerosol mist is drawn into the isolated inner cylinder 26 and through the metallic wool filler 30 without contacting the grounded outer cylinder 24. Once the charge inside of inner cylinder 26 has reached a steady state condition, a current flow path to the outer cylinder 24 is established via wire 38 connected to a feedback resistor 110 of a current-to-voltage converter 112. Since the output of the current-to-voltage converter 112 is of a very low magnitude normally in the range of picoamperes, the output is fed through a selectible gain amplifier 114. Since leakage currents of the current-to-voltage converter 112 produce offset error that may be significant when amplified by 100 or 1000 as is the case for the more sensitive scales of the selectible gain amplifier 114, the offset error is compensated for by an automatic bias offset correction loop 116 which maintains the amplifier output at zero for slow random changing bias currents that may produce the offset error. The bias offset correction loop 116 is opened by a sample and hold 118 during the measurement period. The integrator 120 eliminates the slow random changes that would cause the offset error. The read switch 122 is the previously mentioned switch that is closed during the sampling process. Closing of the read switch 122 opens the bias offset correction loop 116 to give an output from the amplifier 114.

Figure 9:
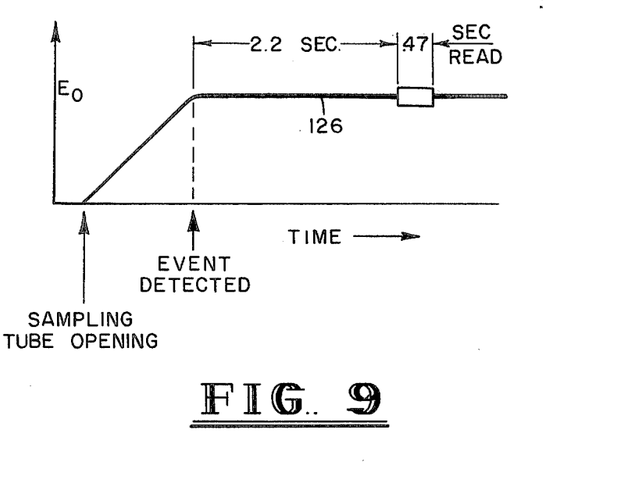
FIG. 9 is a timing diagram showing charge collected inside of the charge density meter during measuring as a function of time after the opening of the intake sampling valve.

When the intake sampling passages 96 are opened and a charged aerosol mist is drawn into the inner cylinder 26, the charge being measured varies with time as shown in FIG. 9. An event detector, timer, control readout 124 (FIG. 9) detects the point at which the charge represented by waveform 126 of FIG. 9 levels off. Approximately 2.2 seconds after the waveform 126 levels off, a sample of the output voltage is taken for approximately 0.47 seconds. At the end of the 0.47 seconds, the voltage measured during that interval will appear on the digital readout meter 128. The light emitting diode 130 previously referred to hereinabove will automatically turn OFF and the operator may then release the outer tube 80 and open the read switch 122.

During periods of nonsampling, air from other than the tank is continuously drawn through the electrostatic charge density meter by a vacuum source. It is important that the air intake holes 90, circulating openings 88, and intake sampling passages 96 by designed so that the air flow between the sampling and nonsampling modes of operation is equal. The turbine 106 mounted in the exhaust stream behind the metallic wool filler 30 is used to generate an AC voltage by means of a magnetic pickup with the frequency at the turbine output 108 being proportional to the volume flow rate through the electrostatic charge density meter 10. A typical relationship for determining the flow rate is as follows:

$$Q = 0.1 f + 2$$

where: Q=the flow rate in meters$^3$/minute and f is the flowmeter frequency in Hertz.

The parameters required in determining the electrostatic charge density include: (1) the voltage reading $E_0$; (2) the flow rate Q through the electrostatic charge density meter 10; (3) the value of the feedback resistor 110 in the current-to-voltage converter 112; (4) the gain setting G of the selectible amplifier 114; and (5) the efficiency k of the metallic wool filler 30 to collect the charge thereon. These parameters may be used to determine charge density as follows:

$$\rho = \frac{KE0}{QRG} \text{ coulombs/m}^3.$$

The efficiency of the metallic wool filler 30 is expressed in percentage and is an experimental parameter that must be determined by calibration of the electrostatic charge density meter by using an aerosol mist of known charge density.

DETAILED DESCRIPTION OF ELECTRONIC CIRCUIT

Figure 6:
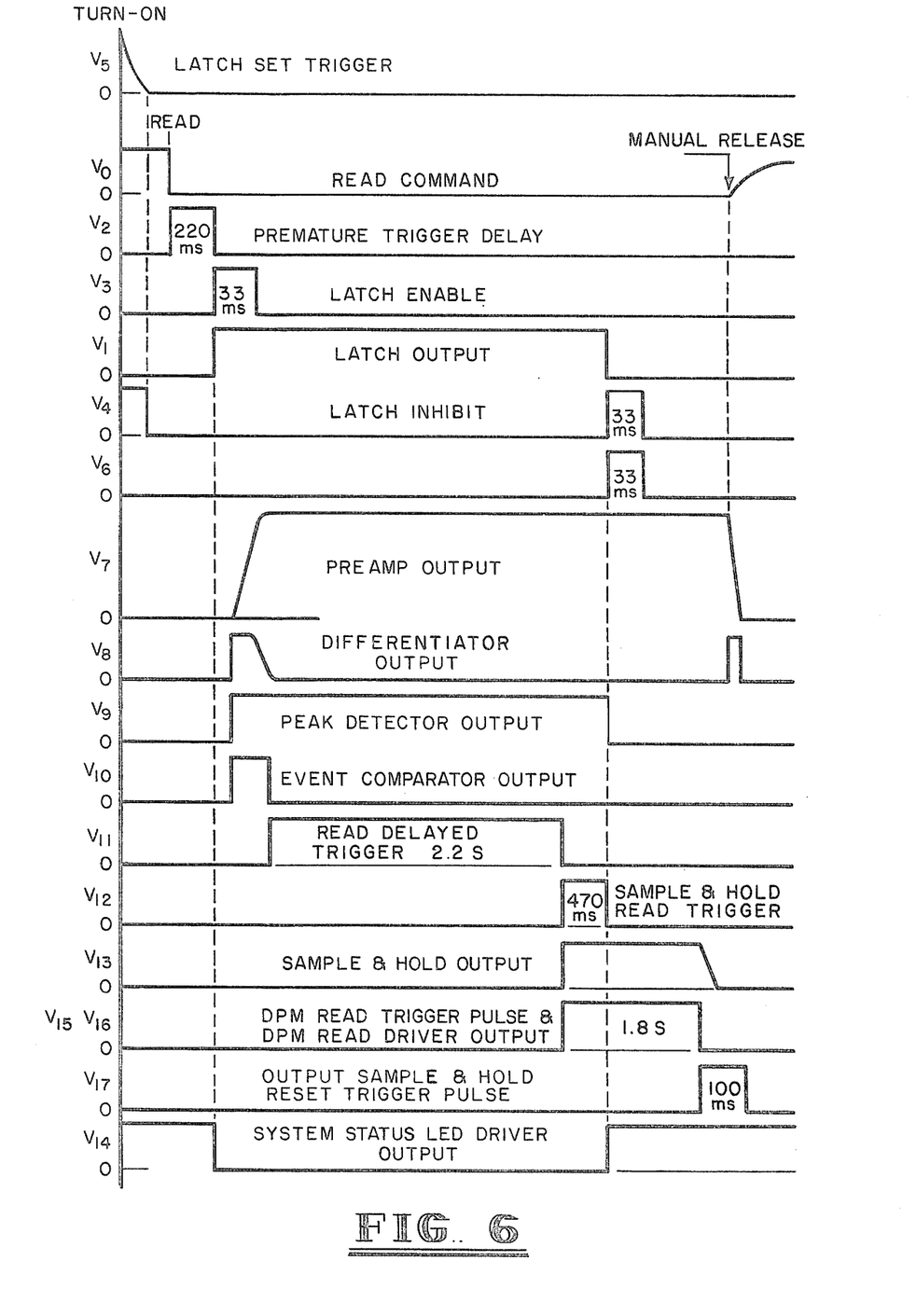
FIG. 6 is a logic timing diagram showing waveforms that occur in FIGS. 5a and 5b during momentary sampling.
Figure 7:
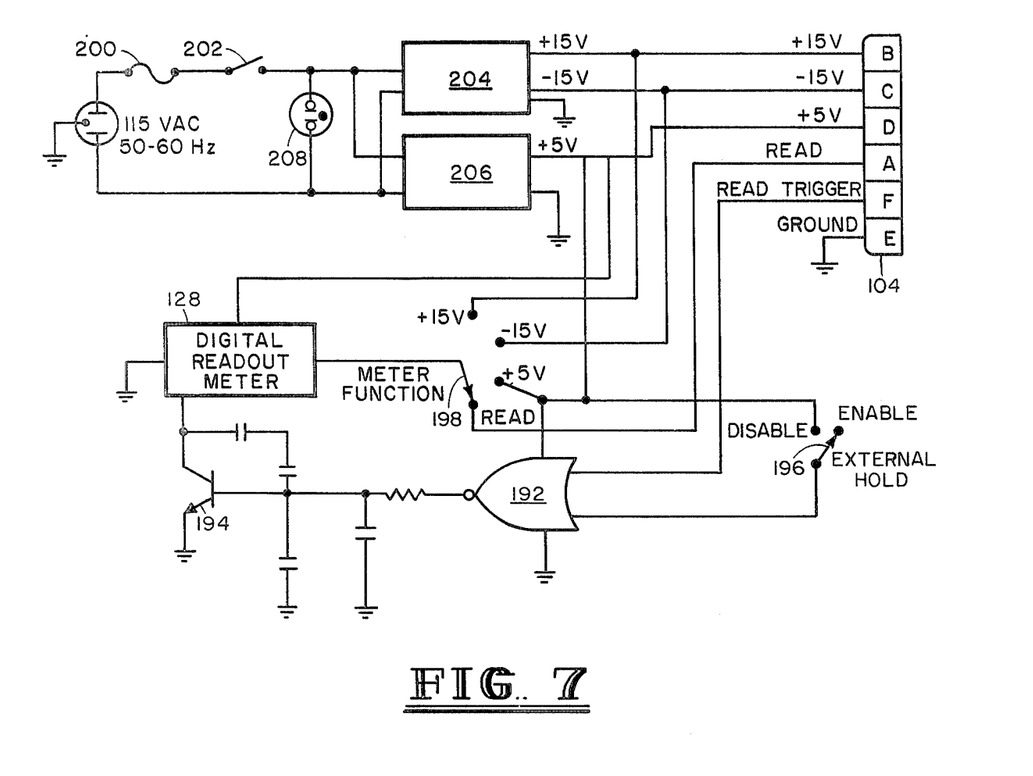
FIG. 7 shows the schematic diagram for the power supply and digital meter indicator.

The electronics of the present invention has four subsystems which include: (1) the sensitive ammeter 42; (2) logic circuits; (3) digital readout meter 128; and (4) a power supply. The sensitive ammeter 42 and logic circuit are contained within the electronic control package 16 and are shown in detail in FIGS. 5a and 5b. Both the sensitive ammeter 42 and the logic circuits are contained in separate shielded compartments to prevent electrostatic interference. FIG. 6 shows logic timing waveforms for the circuitry shown in FIGS. 5a and 5b. FIG. 7 gives the schematic diagram for the power supply and the digital readout meter 128.

Figure 5A:
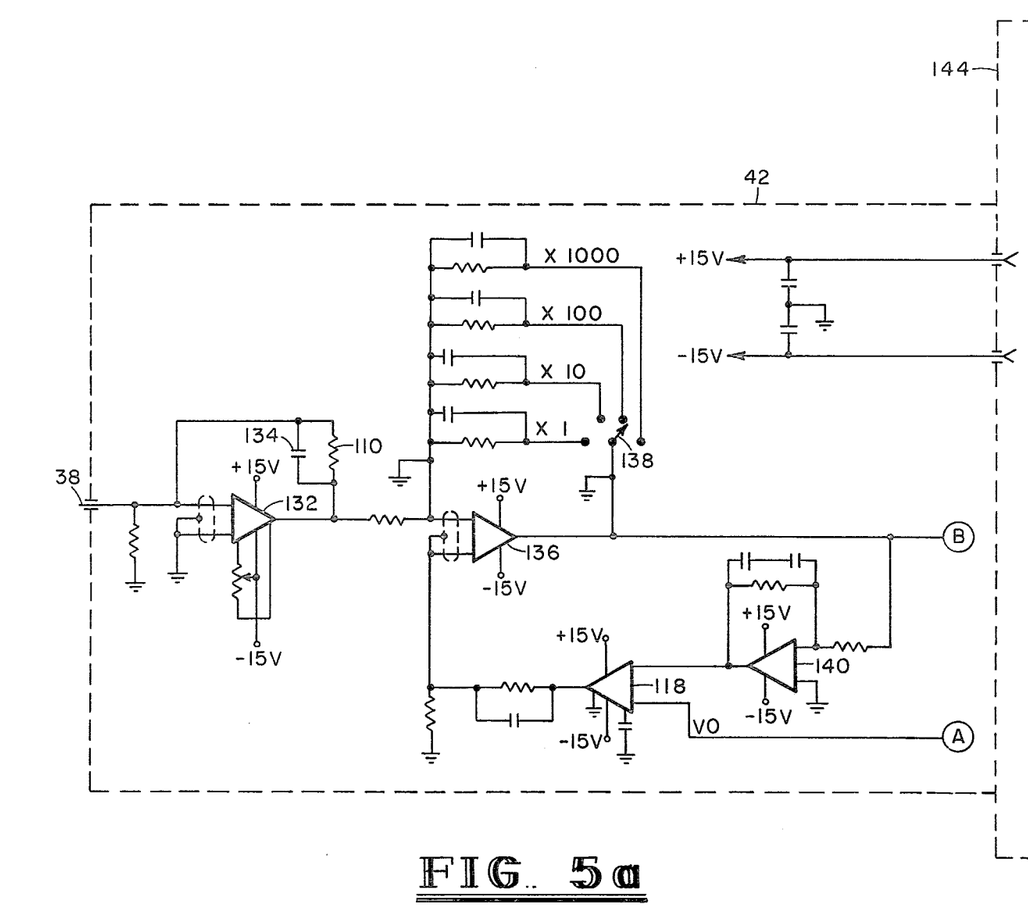
FIGS. 5a and 5b show the schematic diagram for the ammeter and control logic contained in the electronic package shown in FIG. 1.
Figure 5B:
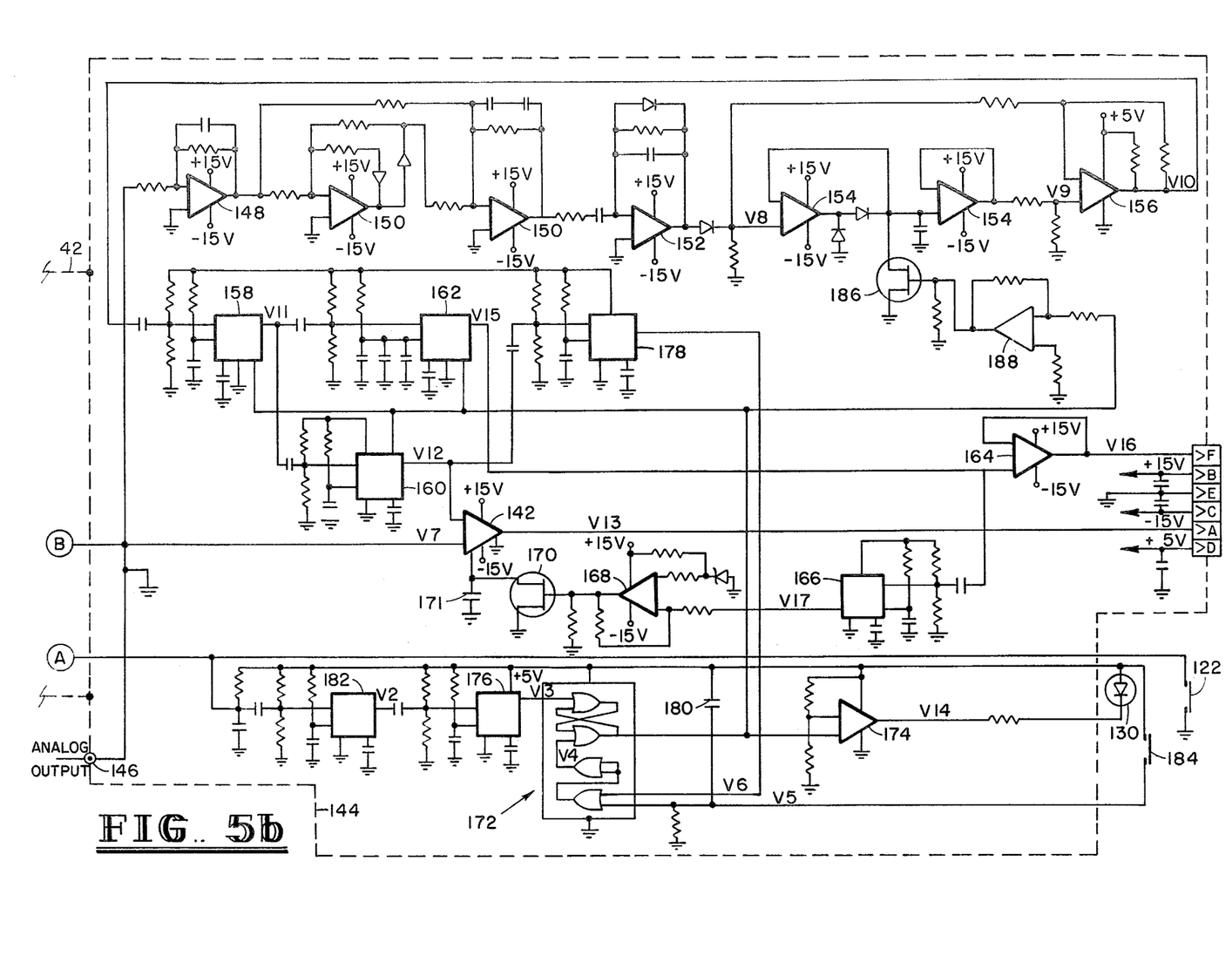

Referring to FIGS. 5a and 5b, the insulated input wire 38 is received inside of the sensitive ammeter 42 by operational amplifier 132. Feedback resistor 110 changes the operational amplifier 132 to the previously described current-to-voltage converter 112. Capacitor 134 in parallel with feedback resistor 110 restricts the band width to less than 2 Hz. The band width of DC to 2 Hz is adequate for detecting the ramp function that occurs when a charged mist is drawn into the inner cylinder 26 of the electrostatic charge density meter 10. An amplifier 136 is used to amplify the output from the operational amplifier 132. Amplifier 136 has a selectible gain switch 138 (also shown in FIG. 1) to allow the gain to be varied by factors of ten. When the output is amplified by 100 or 1000 as determined by the selectible gain switch 138, an offset error may be produced due to slowly changing conditions with time. The bias offset correction loop 116 (previously described in conjunction with FIG. 4) includes an integrator 140 that receives the output signal of amplifier 136 to create an offset voltage equal to the bias offset which is fed back to the input of amplifier 136, thereby always driving the output of amplifier 136 to zero as long as the bias offset correction loop remains connected. To take a reading, the output amplifier is disconnected by a sample-and-hold switch 118 controlled by read switch 122 (FIG. 5b). Under these conditions, short duration measurements can be made without being affected by the slowly changing nature caused by biasing errors.

By use of the bias offset correction loop 116 formed by sample-and-hold switch 118 and integrator 140, currents as low as 0.5 picoamperes can be effectively measured. The upper limit of measurement is restricted only by the value of the feedback resistor 110 and the current-to-voltage converter 112 and supply voltages.

The output of the sensitive ammeter 42 is coupled to the digital readout meter 128 by means of a sample and hold module 142 and the logic section 144. The read time and the duration of the holding voltage are controlled by the logic section 144 and will be described in further detail in the subsequent section.

An analog output 146 (see FIG. 1) is provided for connection to instrumentation monitoring devices, such as a strip chart recorder. A continuous analog signal will be provided at the analog output 146 as long as the read switch 122 is depressed and a charged mist is collected in the metallic wool filler 30.

The purpose of the logic section 144 is to provide a read pulse for the digital readout meter 128 so that a DC voltage can be measured that would indicate a value proportional to the charge density. To accomplish this, the logic section 144 must be able to detect the corner transit event of the output waveform 126 shown in FIG. 9, and then generate a read pulse for the digital readout meter 128 after a specific time delay interval.

Detection of the corner transit event of the output waveform 126 is accomplished by several components with the first component being isolation amplifier 148 that receives the output signal from the sensitive ammeter 42. Since the output of the sensitive ammeter 42 may be either positive or negative, a fullwave rectifier 150 provides a single polarity for differentiator 152 in the peak detector combination 154. The output of the differentiator 152 always has a positive polarity as required by the peak detector 154. The input and the output of the peak detector 154 are then connected to the inputs of comparator 156. In operation, the output of the comparator 156 will switch from a zero state to a high state when the differentiator 152 detects the presence of the initial ramp function from the output of the sensitive ammeter 42. The output of the comparator 156 will remain high until the slope of the output waveform 126 (see FIG. 9) approaches zero. When this occurs, the comparator 156 will switch logic states. The negative transition of the output of the comparator 156 is used to trigger a delay timer described hereinbelow. The output waveforms for the differentiator 152, peak detector combination 154, and the comparator are waveforms $V_8$, $V_9$ and $V_{10}$, respectively in FIG. 6. Waveform $V_7$ of FIG. 6 shows a typical output of the sensitive ammeter 42.

After the comparator 156 switches logic states, the logic circuitry will sample and read the output of the sensitive ammeter 42 after a 2.2 second delay. This time delay is sufficient for the output waveform from the sensitive ammeter to stabilize before a measurement is made. The time delay is produced by integrated circuit timer 158. The integrated circuit timer 158 generates a pulse (waveform $V_{11}$ shown in FIG. 6) whenever the input switches from the high state to the low state, which pulse is used to generate other timing pulses and sequences as shown in FIG. 6. The output $V_{11}$ of the integrated circuit timer 158 generates a delay pulse through the sample and hold module 160. The output for the sample and hold module 160 is shown as waveform $V_{12}$ in FIG. 6 and is for approximately 0.47 seconds.

A second delay pulse is generated by digital readout meter trigger 162, which is operated concurrently with the sample and hold module 160. The output from digital readout meter trigger 162 feeds amplifier 164, which drives the digital readout meter 128 through a cable (not shown) connected therebetween. When the output of the digital readout meter trigger 162 changes state as represented by waveform $V_{15}$, the count contained in the digital readout meter 128 is stored, and a 100 millisecond pulse is generated by sample and hold trigger 166 that drives amplifier 168. The output of amplifier 168 drives FET switch 170 which, when waveform $V_{17}$ from sample and hold trigger 166 becomes positive, provides a low impedance discharge path across the holding capacitor 171.

The integrated circuit timer 158, sample and hole module 160, digital output meter trigger 162 described above must have their input lines at a high logic state before they will operate. A latch 172 is used to control the logic state for the input reset lines to eliminate premature false triggering from initial transients, or false pulses that would occur after the transit event of output waveform 126. The output of latch 172 provides a means for visually displaying the status of the measurement cycle by light emitting diode 130 driven by LED driver 174. The light emitting diode 130 turns OFF when the latch is released and the measuring cycle is complete. The latch 172 is made from a combination of NOR gates. The output of the latch 172 must be a low state to disable the various timers, a condition which is satisfied when both inputs are in a low state. The first input is received through a latch enable 176, which assumes a low state when power is applied. To satisfy initial turn-on conditions, the latch reset trigger 178 must have a high output which is fed to latch 172. Also, capacitor 180, which is connected to a supply voltage, has to be charged. Whenever a positive pulse is applied to either the inputs as indicated by waveforms $V_5$ and $V_6$ in FIG. 6, the latch 172 will switch states.

When the read switch 122 is closed, delay premature trigger 182 will generate a pulse of approximately 0.22 seconds duration. Thereafter, latch enable 176 generates a 33 millisecond pulse to enable the latch 172, integrated circuit timer 158, digital readout meter trigger 162, and sample-and-hold module 160 to stabilize. The delay premature trigger 182 of 0.22 seconds eliminates any transits that can be amplified by amplifier 136 and detected by the comparator 156 when the bias offset correction loop 116 is opened.

Figure 8:
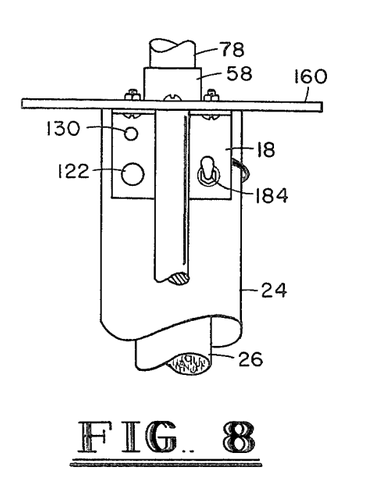
FIG. 8 is a partial top view of FIG. 1 showing the operator controls of the charge density meter.

If, for any reason, the read switch 122 is closed and then released, it is necessary to reset the latch 172 before proceeding with the measurement. This may be accomplished by the reset switch 184 located on the indicator panel 18 with the read switch 122 and light emitting diode 130 as shown in FIG. 8. The closing of the reset switch 184 changes the output of the latch 172 to the low state so that a new read cycle may be initiated by the closing of read switch 122.

Once the complete timing and read cycle has occurred, and the output of the sensitive ammeter 42 is stored in the digital readout meter 128, latch reset trigger 178 will generate a latch reset pulse shown as waveform $V_6$ in FIG. 6. The latch reset trigger 178 is actuated by the sample-and-hold module 160 as it changes states. The latch reset trigger 178 provides a pulse to reset latch 172. The output from latch 172 connects to LED driver 174, which will turn ON the light emitting diode 130 approximately 0.22 seconds after the read command is given by the read switch 122, and will turn OFF 2.67 seconds after the event has been detected. After the light emitting diode 130 turns OFF, the operator may release the read switch 122.

The latch output is also used to discharge the FET switch 186 of peak detector 154 through reset driver 188. When the output of latch 172 is in a low state, FET switch 186 is turned ON and provides a low impedance discharge path across capacitor 190. When the output voltage of latch 172 is high, the resistance of FET switch 186 is essentially an open circuit.

Referring now to FIG. 7, a power supply and digital readout meter are shown and connected as provided by connector 104 previously discussed in conjunction with FIG. 1. The digital readout meter 128, while it may be of any particular type, a Fairchild Model 320350 VPM was found to be particularly well suited because of its external hold feature. As previously explained in conjunction with FIGS. 5a and 5b, the logic section 144 turns the digital readout meter 128 ON for a period of 1.8 seconds and then holds the final reading at the end of that time period. External circuitry is required to give the external hold feature as shown in FIG. 7. The external circuitry includes a NOR gate 192, which is used to drive NPN transitor 194. The digital readout meter 128 will operate normally when transistor 194 is turned ON and will continuously update its voltage reading about three times per second. To hold the final reading, transistor 194 is switched OFF by applying a low logic state to its input by NOR gate 192.

The logic state of transistor 194 is controlled by NOR gate 192 and external hold switch 196. When operating normally for charge density measurements, the external hold switch 196 is in the ENABLE position allowing read and hold functions to be controlled automatically from the logic section 144. Alternatively, when the external hold switch 196 is in the DISABLE position, the digital readout meter 128 will operate continuously to allow the three power supply voltages used in the instrument to be checked by meter switch 198. Meter switch 198 must be changed to the READ position for making charge density measurements.

Standard voltages of +15 volts, −15 volts and +5 volts are used by the digital readout meter 128, the sensitive ammeter 42, and the logic section 144. From an input line voltage of 115 volts AC, 50–60 Hz, power is connected through one amp fuse 200 and power switch 202. Standard off-the-shelf power modules 204 and 206 are used to supply the voltages of +15 volts, −15 volts and +5 volts. Pilot light 208 indicates if the power switch 202 is closed.

Figure 10:
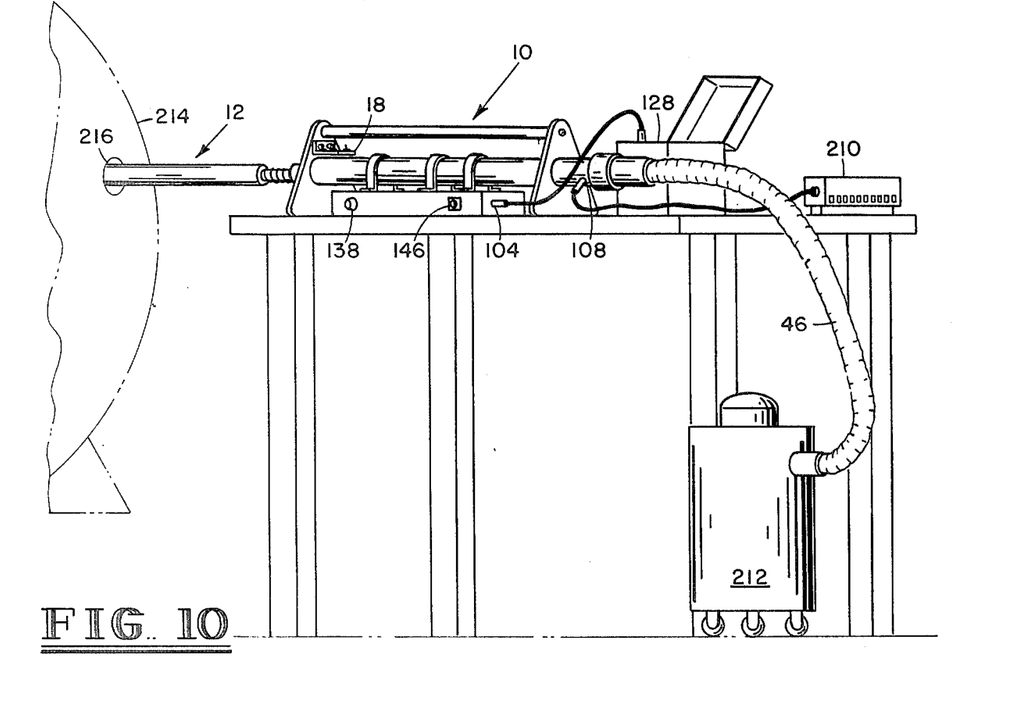
FIG. 10 is an environmental view of the present invention during the laboratory testing.

An environmental view showing the electrostatic charge density meter 10 and sampling tube 12 being used in a laboratory is illustrated in FIG. 10 The turbine output 108 is connected to a frequency meter 210 and connector 104 is connected to the power supply/digital readout meter 128. Also, the flexible hose 46 is connected to a vacuum source 212. By insertion of the sampling tube 12 inside of the enclosed area 214 through a suitable opening 216, the electrostatic charge density inside of the enclosed area 214 can be measured without any substantial change or effect on the overall electrostatic charge density. In practical application, the enclosed area 214 may be the tank of a ship. By insertion of the sampling tube 12 through an opening 216, which may have porthole cover, an individual can measure the electrostatic charge density inside of the tank.

Figure 11:
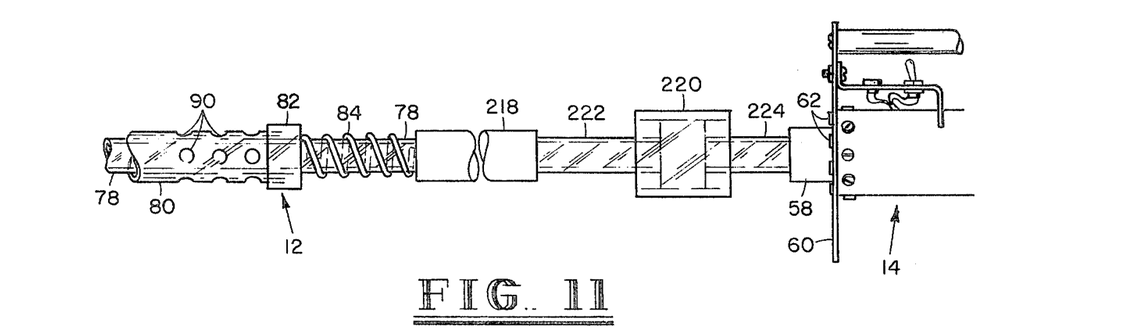
FIG. 11 is a partial elevated view showing an alternative type sampling tube.

FIG. 11 is an alternative embodiment for the sampling tube 12 wherein an elongated plastic tubing 218 several feet in length is connected to the inner tube 78 of the sampling tubing 12. Thereafter, a water trap 220 is connected between tubing 222 and 224. Tubing 224 connects to intake flange in the manner previously described for inner cylinder 78 in conjunction with FIG. 1. The purpose of the water trap 220 is to prevent water droplets which form on the walls of the sampling tube 12 from eventually collecting in the metallic wool filler 30 and the inner cylinder 26 in such a manner that it may bridge the insulator 64 or insulated flange connector 52.

It is important that the air flow through the sampling tube 12 be equalized between the sampling and the nonsampling operating states. Therefore, it may be necessary to adjust the number and the size of either the air intake holes 90, circulating openings 88, or intake sampling passages 96. Fine adjustments may be made to equalize the air flow by partially opening or closing some of these passages.

The sampling tube 12 in the preferred embodiment was made from a nonconductive clear Lucite plastic that could be easily disassembled for cleaning and inspection.

The turbine 106 is used to measure the air flow through the electrostatic charge density meter 10. The turbine 106 is calibrated to determine the exact relationship between the output frequency of turbine output 108 and the flow rate in cubic feet per minute.

I claim:

1. An electrostatic charge density measuring device for measuring electrostatic charge density of a charged atmosphere comprising:
    electrically insulated chamber means;
    conduit means for circulating an uncharged atmosphere through said chamber means;
    valve means connected to said conduit means for temporarily changing circulation through said conduit means and through said chamber means from said uncharged atmosphere to said charged atmosphere, said valve means being located in said charged atmosphere at least during said measuring, both said valve means and said conduit means being electrically nonconductive to minimize electrical effect on said charged atmosphere;
    capacitor means formed between said chamber means and ground means, said charged atmosphere circulating through said chamber means to charge said capacitor means from said electrostatic charge; and
    control means for measuring current flow from said capacitor means as caused by said electrostatic charge and converting said measured current to charge density of said charged atmosphere.

2. The electrostatic charge density meter as given in claim 1 wherein said capacitor means includes concentric cylinders with an inner cylinder forming said chamber means and being electrically insulated from said outer cylinder, said inner cylinder being filled with a porous conductive wool filler.

3. The electrostatic charge density meter as given in claim 1 further comprises a sampling tube, said valve means being on a first end of said sampling tube and a second end of said sampling tube being in fluid connection with said chamber means, said sampling tube forming at least a part of said conduit means.

4. The electrostatic charge density meter as given in claim 3 wherein said sampling tube includes concentric tubes with a first passage for said charged atmosphere being near said first end of said sampling tube and a second passage for said uncharged atmosphere being near said second end of said sampling tube, said sampling tube being adapted for extension inside of an enclosed area before opening of said second passage which forms a part of said valve means.

5. The electrostatic charge density meter as given in claims 1, 2, 3 or 4 includes blower means connected to said chamber means for creating a vacuum therein, said vacuum alternately drawing said uncharged atmosphere and said charged atmosphere through said chamber means.

6. The electrostatic charge density meter as given in claim 5 including means for monitoring flow through said chamber means created by said vacuum.

7. The electrostatic charge density meter as given in claim 3 wherein said sampling tube includes a water trap therein to prevent liquids from reaching said chamber means in sufficient quantities to cause an electrical short.

8. A control circuit for measuring electrostatic charge density of a charged atmosphere circulated through an electrically isolated chamber, said control circuit comprising:
    current-to-voltage converter connected to said isolated chamber for measuring current from said isolated chamber to ground;
    event detector means connected to an output of said current-to-voltage converter for generating an event output when said current has stabilized;
    timer means connected to said event detector means for generating a time delayed output upon receiving said event output;
    control means connected to said timer means for generating a readout signal upon expiration of said time delayed output; and
    readout means connected to said control means and said current-to-voltage converter for receiving said readout signal and said current-to-voltage converter output, said readout means giving charge density of said charged atmosphere upon receiving said readout signal.

9. The control circuit as given in claim 8 comprising amplifier means for increasing said output of said current-to-voltage converter prior to being received by said event detector and said readout means.

10. The control circuit as given in claim 9 comprising bias offset correction loop connected to an input and output of said amplifier means, said bias offset correction loop having integrator means to prevent slow variations in said output of said amplifier caused by current drift at higher amplification settings.

11. The control circuit as given in claim 10 wherein said bias offset correction loop includes integrator means, sample-and-hold means in said bias offset correction loop to maintain a given reading for said charge density until reset by reset means.

12. The control circuit as given in claim 8 wherein said control means includes enable means to allow said readout signal upon a set of predetermined conditions having been met.

13. The control circuit as given in claim 12 including means for resetting said control circuit to make another measurement.

14. The control circuit as given in claim 8 wherein said readout means includes digital display means for indicating charge density in coulombs per cubic meter.

15. The control circuit as given in claim 8 comprises power supply means for said circuit means, said power supply means having switchable meter function so that said charge density or various voltages necessary for said control circuit may be visually indicated.

16. The control circuit as given in claim 8 comprising detector means for generating a flow event signal when said charged atmosphere passes through said isolated chamber, said flow event signal serving to indicate stabilized flow through said isolated chamber.

17. A method of measuring charge density of a charged atmosphere in an area consisting of the following steps:
   first circulating uncharged gases through an insulated conductive inner chamber;
   opening valve means in said area to simultaneously terminate said first circulating of said uncharged gases and begin second circulating of said charged atmosphere through said inner chamber for a short time period;
   measuring current flow from said inner chamber to an outer conductive surface adjacent thereto at a predetermined interval during said short time period, said predetermined interval being after stabilization of said measured current flow; and
   converting said measured current flow to charge density.

18. The method as given in claim 17 includes a first step of resetting a control circuit, said measuring step and said converting step being performed by said control circuit.

19. The method as given in claim 18 includes before said opening step a step of inserting a sampling tube inside of said area, said sampling tube being of nonconductive material.

20. The method as given in claim 19 wherein said opening step includes moving an outer tube of said sampling tube with respect to an inner tube during a sampling period, and subsequently releasing said outer tube for return of said outer tube to its original position.

21. The method as given in claim 17 includes a continuous step of monitoring flow through said inner chamber during sampling.

22. The method as given in claim 17 wherein said converting step includes giving a visual indication of said charge density.

23. The method as given in claim 17 consisting of an initial step of calibration fluid flow through said inner chamber, current measuring equipment and converting equipment against known fluids.

24. The method as given in claim 17 including removing enough liquids from said uncharged gases and said unknown atmosphere prior to entry into said inner chamber to prevent electrical shorts.

* * * * *